(12) United States Patent
Ferrone et al.

(10) Patent No.: US 6,939,948 B1
(45) Date of Patent: Sep. 6, 2005

(54) GD2 PEPTIDE MIMICS

(75) Inventors: Soldano Ferrone, Buffalo, NY (US); Chun-Yen Tsao, Grand Island, NY (US); Xinhui Wang, Williamsville, NY (US); Wei Luo, Getzville, NY (US); Nai-Kong V. Cheung, Purchase, NY (US)

(73) Assignees: Health Research, Inc., Buffalo, NY (US); Sloan Kettering Institute for Cancer Research, New York, NY (US)

( * ) Notice: Subject to any disclaimer, the term of this patent is extended or adjusted under 35 U.S.C. 154(b) by 4 days.

(21) Appl. No.: 10/395,434

(22) Filed: Mar. 24, 2003

Related U.S. Application Data
(60) Provisional application No. 60/366,558, filed on Mar. 22, 2002.

(51) Int. Cl.[7] .......................... C07K 5/00; A61K 38/00
(52) U.S. Cl. .......................... 530/326; 530/300; 514/2; 514/14
(58) Field of Search .......................... 424/130.1, 184.1; 530/300, 326, 327, 387.1

(56) References Cited

U.S. PATENT DOCUMENTS

| | | | |
|---|---|---|---|
| 5,807,978 A | * | 9/1998 | Kokolus et al. |
| 5,882,654 A | * | 3/1999 | Morton |

OTHER PUBLICATIONS

Chapman et al., *Vaccination with a Bivalent GM2 and GD2 Ganglioside Conjugate Vaccine: A Trial Comparing Doses of GD2–Keyhole Limpet Hemocyanin*, Clinical Cancer Research (Dec. 2000) vol. 6, pp. 4658–4662.

Cheung et al., *Induction of Ab3 and Ab3' Antibody was Associated with Long–Term Survival after Anti–GD2 Antibody Therapy of Stage 4 Neuroblastoma*, Clinical Cancer Research (Jul. 2000) vol. 6, pp. 2653–2660.

Kramer et al., *Disialoganglioside GD2 Loss Following Monoclonal Antibody Therapy is Rare in Neuroblastoma*, Medical and Pediatric Oncology (2001) vol. 36, pp. 194–196.

Kushner et al., *Phase II Trial of the Anti–GD2 Monoclonal Antibody 3F8 and Granulocyte–Macrophage Colony–Stimulating Factor for Neuroblastoma*, Journal of Clinical Oncology (Nov. 15, 2001) vol. 19, No. 22, pp. 4189–4194.

Murray et al., *Phase I Trial of Murine Monoclonal Antibody 14G2a Administered by Prolonged Intravenous Infusion in Patients with Neuroectodermal Tumors*, Journal of Clinical Oncology (Jan. 1994) vol. 12, No. 1, pp. 184–193.

Qiu et al., *Towards the Development of Peptide Mimotopes of Carbohydrate Antigens as Cancer Vaccines*, Hybridoma (Nov. 1, 1999) vol. 18, pp. 103–112.

Saleh et al., *Phase 1 Trial of the Murine Monoclonal Anti–GD2 Antibody 14G2a in Metastatic Melanoma*, Cancer Research (Aug. 15, 1992) vol. 52, pp. 4342–4347.

Slart et al., *An Animal Model of Pain Produced by Systemic Administration of an Immunotherapeutic Anti–Ganglioside Antibody*, Pain (1997) vol. 69, pp. 119–125.

Sorkin et al., *Antibody Directed Against GD2 Produces Mechanical Allodynia, but Not Thermal Hyperalgesia when Administered Systemically or Intrathecally Despite its Dependence on Capsaicin Sensitive Afferents*, Brain Research (2002) vol. 930, pp. 67–74.

Tai et al., *Immunogenicity of Melanoma–Associated Gangliosides in Cancer Patients*, Int. J. Cancer (1985) vol. 35, pp. 607–612.

Yu et al., *Phase 1 Trial of a Human–Mouse Chimeric Anti–Disialoganglioside Monoclonal Antibody ch14.18 in Patients with Refractory Neuroblastoma and Osteosarcoma*, Journal of Clinical Oncology (Jun. 1998) vol. 16. No. 6, pp. 2169–2180.

* cited by examiner

*Primary Examiner*—Larry R. Helms
*Assistant Examiner*—David J. Blanchard
(74) *Attorney, Agent, or Firm*—Hodgson Russ LLP

(57) ABSTRACT

The present invention provides peptide mimics for GD2 ganglioside. The peptide mimics were identified by panning phage display peptide libraries with an anti-GD2 monoclonal antibody. The identified peptide mimics can be used as immunogens for cancer therapy such as for melanoma and neuroblastoma.

3 Claims, 1 Drawing Sheet

SEQUENCE LISTING

```
<160> NUMBER OF SEQ ID NOS: 9

<210> SEQ ID NO 1
<211> LENGTH: 12
<212> TYPE: PRT
<213> ORGANISM: artificial sequence
<220> FEATURE:
<223> OTHER INFORMATION: J83 peptide mimic for GD2

<400> SEQUENCE: 1

Glu Cys Val Glu Gln Gly Lys Phe Met Tyr Cys Ala
                5                   10

<210> SEQ ID NO 2
<211> LENGTH: 12
<212> TYPE: PRT
<213> ORGANISM: artificial sequence
<220> FEATURE:
<223> OTHER INFORMATION: J8C peptide mimic for GD2
```

```
<400> SEQUENCE: 2

Lys Cys Asp Pro Tyr Thr Leu His His Tyr Cys Trp
                 5                  10

<210> SEQ ID NO 3
<211> LENGTH: 12
<212> TYPE: PRT
<213> ORGANISM: artificial sequence
<220> FEATURE:
<223> OTHER INFORMATION: J8D peptide mimic for GD2

<400> SEQUENCE: 3

Ser Cys Leu Glu Gln Glu Lys Trp Tyr Gly Cys Ile
                 5                  10

<210> SEQ ID NO 4
<211> LENGTH: 12
<212> TYPE: PRT
<213> ORGANISM: artificial sequence
<220> FEATURE:
<223> OTHER INFORMATION: J8G peptide mimic for GD2

<400> SEQUENCE: 4

Tyr Cys Thr Pro Tyr Asp Val Ser Ile Gly Cys Arg
                 5                  10

<210> SEQ ID NO 5
<211> LENGTH: 15
<212> TYPE: PRT
<213> ORGANISM: artificial sequence
<220> FEATURE:
<223> OTHER INFORMATION: J51 peptide mimic for GD2

<400> SEQUENCE: 5

Asp Cys Phe Arg Gly Asp Pro Tyr Gln Pro Lys Trp Arg Leu Cys
                 5                  10                  15

<210> SEQ ID NO 6
<211> LENGTH: 15
<212> TYPE: PRT
<213> ORGANISM: artificial sequence
<220> FEATURE:
<223> OTHER INFORMATION: J50 peptide mimic for GD2

<400> SEQUENCE: 6

Ser Leu Pro Glu Asp Arg Tyr Glu Asp Gly Trp Ile Phe Lys Pro
                 5                  10                  15

<210> SEQ ID NO 7
<211> LENGTH: 15
<212> TYPE: PRT
<213> ORGANISM: artificial sequence
<220> FEATURE:
<223> OTHER INFORMATION: J10ab peptide mimic for GD2

<400> SEQUENCE: 7

Ala Cys Arg Glu Gly Pro Pro Tyr Tyr Tyr Phe Cys Pro Ser Leu
                 5                  10                  15

<210> SEQ ID NO 8
<211> LENGTH: 15
<212> TYPE: PRT
<213> ORGANISM: artificial sequence
<220> FEATURE:
<223> OTHER INFORMATION: J2gh peptide mimic for GD2
```

-continued

```
<400> SEQUENCE: 8

Pro Thr Gly Arg Cys Glu Val His Cys Ser Asn Ser Asn Thr Thr
                5                  10                  15

<210> SEQ ID NO 9
<211> LENGTH: 20
<212> TYPE: DNA
<213> ORGANISM: artificial sequence
<220> FEATURE:
<223> OTHER INFORMATION: primer

<400> SEQUENCE: 9
gccaatagta gcaccaacga                                          20
```

GD2 PEPTIDE MIMICS

This application claims the priority of U.S. provisional application Ser. No. 60/366,558 filed on Mar. 22, 2002, the disclosure of which is incorporated herein by reference.

This work was supported by Grant no. CA 37959 from the National Institute of Health. The Government has certain rights in the invention.

FIELD OF THE INVENTION

This invention relates generally to the field of peptide mimics and more particularly to provides peptides mimics corresponding to the GD2 ganglioside.

BACKGROUND OF THE INVENTION

In North America, lung carcinoma and melanoma were considered to be the second and sixth common cancer in 2002, and neuroblastoma is the most common extracranial solid tumor of childhood. Currently, all stage survival rate is 15% in lung carcinoma, 89% in melanoma patients and 80% in neuroblastoma patients in North America. Current therapy approaches include radiation and chemotherapy. However, the poor survival rates underscore the need for developing new approaches. Also, a new cancer therapy is needed to prevent the relapse of tumors after conventional treatments, and improve the low survival rate of lung carcinoma patients, late stage melanoma patients (12% at the stage IV), and late stage neuroblastoma patients.

A lack of effective radiation therapy and chemotherapy of metastatic melanoma (Philip, et al. 2000) has led to interest in developing immunotherapy of melanoma. For developing tumor vaccines of melanoma, two major approaches have been used: 1) immunizations with whole tumor cell extracts or irradiated tumor cells (Takashi, et al. 1999; Hsuch, 2001); 2) immunizations with melanoma associated antigens such as MART-1 or gp100 (Chianese-Bullock, et al. 2002).

Useful targets for developing immunological approaches include gangliosides. One such ganglioside is GD2. The GD2 ganglioside is a self-glycol-lipid antigen. It is usually low or non-immunogenic in humans. This antigen is over-expressed in human melanoma and neuroblastoma lesions, and has a restricted distribution in normal tissues. Previous clinical trials have suggested that GD2 ganglioside appears to be poorly immunogenic in humans. In some clinical trials, a kind of antigen mimics, anti-idiotypic antibody, has been shown to be able to induce anti-GD2 ganglioside immune responses in neuroblastoma patients. Furthermore, GD2/GD3 peptide mimics have been isolated with anti-GD2/GD3 antibody ME36,1 (Qiu et al., 1999).

Anti-GD2 ganglioside monoclonal antibodies have been utilized in immunotherapy of melanoma. In human clinical trials, anti-GD2 ganglioside monoclonal antibodies have been shown to be effective in either melanoma or neuroblastoma patients (Saleh, et al. 1992; Murray, et al. 1994; Yu, et al. 1998; Cheung, et al. 2000; Kushner, et al. 2001). However, these clinical trials also suggest that the dose-dependent side effects can limit the usage of anti-GD2 antibodies (Saleh, et al. 1992). These side effects include severe generalized pain, hyponatremia, fever, rash, paresthesias, weakness, and chronic refractory postural hypotension (Murray, et al. 1994; Slart, et al. 1997; Yu, et al. 1998; Sorkin, et al. 2002). Furthermore, the recurrence of neuroblastoma in patients after treatment with anti-GD2 ganglioside antibodies is common (62 out of 95 patients) (Kramer, et al. 2001). These clinical findings suggest that a low dose, as well as long duration anti-GD2 ganglioside therapy might present an approach to overcome both the severe treatment side effects and potential post-treatment relapse.

Active specific immunotherapy can induce a low dose and long lasting immune response, which may overcome the disadvantages of anti-GD2 ganglioside antibody therapy for melanoma patients. However, GD2 ganglioside is weakly immunogenic, and the antibody responses to GD2 ganglioside are often of the IgM isotype in humans (Tai, et al. 1985). These are most likely due to the lack of a T helper response and/or tolerance to GD2 ganglioside because it is both a self-antigen and a glycolipid antigen. In order to increase the immunogenicity of GD2 ganglioside, GD2 ganglioside has been conjugated with keyhole limpet hemocyanin (KLH). 45% of patients immunized with the conjugate and QS-21 adjuvant developed either anti-GD2 ganglioside IgM or IgG antibody responses with only grade II toxicity. These include local toxicity at the vaccine sites, fatigue, flu-like symptoms, fever, or headache (Chapman, et al. 2000). However, 55% of immunized patients still did not respond to the GD2-KLH conjugates.

Accordingly, there is an ongoing need to develop new immunotherapeutic approaches to cancers such as melanoma, neuroblastoma lung carcinoma.

SUMMARY OF THE INVENTION

The present invention provides methods of using compositions which elicit an immune response against a tumor associated antigen that is not normally immunogenic. The method comprises using peptide mimics to a ganglioside, GD2, to elicit an immune response.

Accordingly, in one aspect, the invention provides methods for identifying peptide mimics. The method comprises the steps of screening phage display peptide libraries with antibodies to GD2. The identified peptides are then tested for their ability to elicit an immure response and the ability of those antibodies to against GD2 bearing cells.

In another embodiment, the present invention provides a method for eliciting an immune response in patients with GD2 positive tumors. The method comprises administering a composition effective in stimulating a specific immunological response against the GD2 antigen. These composition(s) comprise a peptide that shares immunological characteristics of GD2. While a detectable immunological response is likely to be beneficial, efficacy can also be deduced by an improvement in symptoms or control of growth of the tumor.

Other embodiments include include methods for treating GD2 bearing tumors in an individual by eliciting an antiGD2 immunological response in the subject. The immunological response can be elicited using any of the peptide mimics to the GD2.

Still other embodiment include preparing a composition for use in the generation of an immune response and in the treatment of tumors bearing GD2. The composition comprises the peptide mimics disclosed herein.

DETAILED DESCRIPTION AND OPERATION

Figure 1:
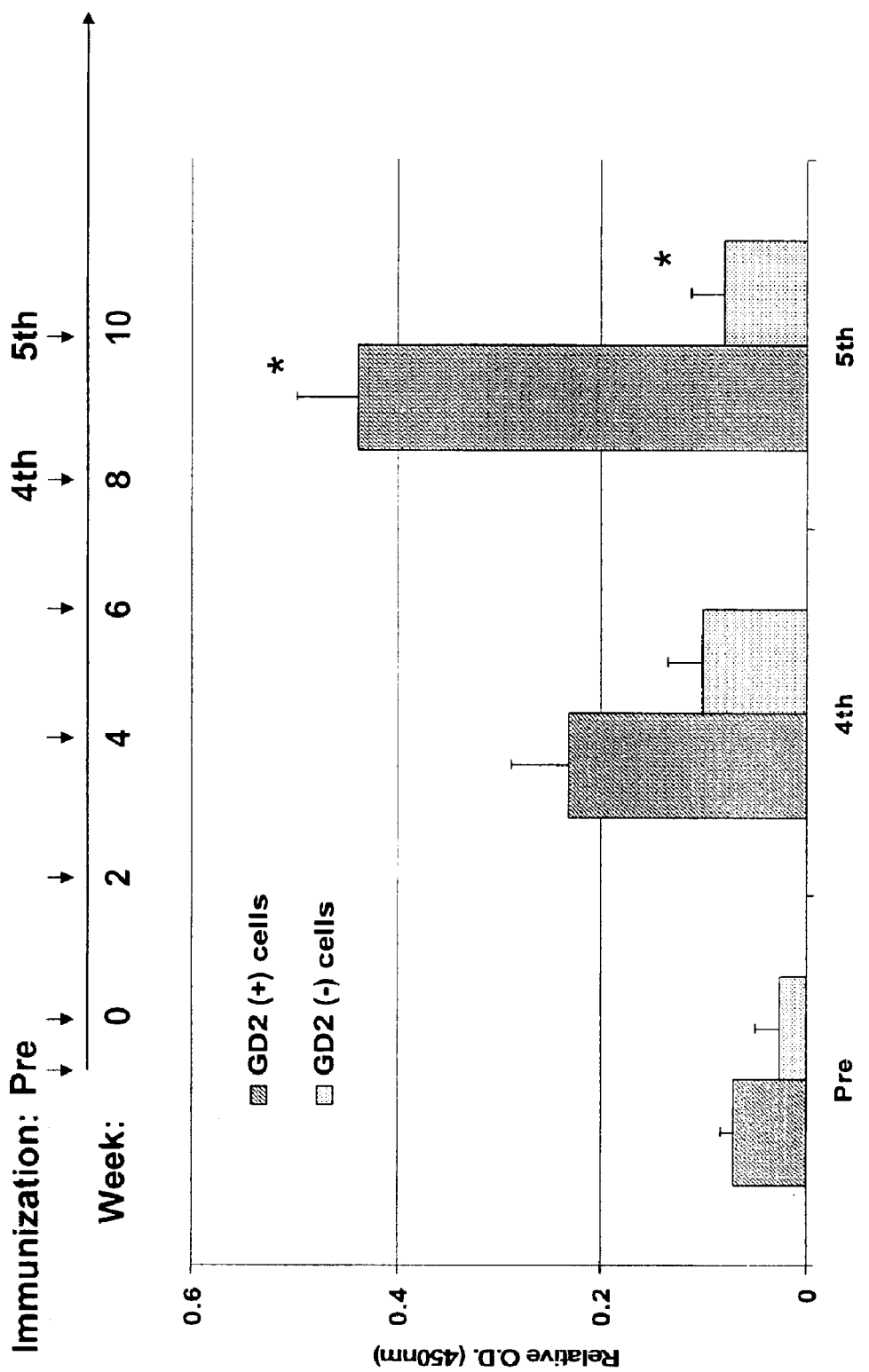
FIG. 1 shows that a peptide of this invention, cJ51 conjugated to Keyhole limpet hemocyanin (KLH) can generate anti-GD2 antibodies Sera obtained from mice after the 5th immunization with the cJ51-KLH (KLH conjugated GD2 peptide mimic cJ51) display a significantly higher reactivity with GD2 (+) cells (IgG responses). The results shown were obtained with sera tested at the dilution 1:30. * indicates P=0.0001, N=10. GD2(+) cells are HTB63 and GD2(−) cells are LG2.

The present invention provides compositions and methods for immunotherapy particularly useful for tumors bearing GD2 ganglioside. The method comprises administering to an individual in need of treatment, a compositions comprising peptide mimics of GD2. The purpose of peptide mimics is to induce immune responses against a tumor-associated antigen (TAA)-GD2 ganglioside, which is usually not immunogenic in human. The peptide mimics can be used for developing a new active immunotherapy of malignancies such as melanoma and neuroblastoma.

Peptide mimics are structurally similar, but not identical, to GD2 ganglioside. Therefore, they may stimulate B cells with low affinities to GD2 ganglioside that survived from the regulation of self-reactive B cells during the establishment of self-identity. Furthermore, it is known that T cell-dependent responses are required to elicit long lasting antibody responses. However, immune responses to GD2 ganglioside are usually T cell-independent, due to lack of presentation of this glycolipid on HLA molecules. Because peptides can be presented on HLA molecules, peptide mimics are more likely to induce T cell-dependent immune responses than GD2 ganglioside. In addition, sequences of peptide mimics may also be utilized for the development of DNA vaccines.

The present invention seeks to overcome some of the drawbacks inherent in the prior art by identifying and isolating peptide/protein antigens that are highly immunogenic in humans. These antigens can then be used to promote specific anti-tumor responses. Peptide mimics have several advantages compare to other antigen mimics such as anti-idiotypic antibodies. First, the production of peptide mimics is easier to be standardized to meet the regulatory requirements for clinical trials. Second, immunization of peptide mimics avoids the induction of antibody responses to the irrelevant part of anti-idiotypic antibodies (Wang, et al. 2001). Third, modification and production of peptide mimics are easier than anti-idiotypic antibodies. This provides advantages when modifying peptide mimics to increase similarities between peptide mimics and GD2 ganglioside, or to increase the presentation of peptide mimics on HLA molecules. Fourth, peptide mimics isolated using different anti-ganglioside antibodies can provide the possibility of generating multiple antigen peptides (MAP), which may induce immune responses against multiple epitopes on GD2 ganglioside or even different TAAs (Qiu, et al. 2000). Fifth, peptide mimics can eliminate side effects due to the infusion of antibodies to patients. Finally, peptide mimics and their sequences can be used to develop dendritic-cell vaccines or DNA vaccines to GD2 ganglioside (Lesinski, et al. 2001). Furthermore, immunogenicity and half life of peptide mimics can be improved by constructing a MAP containing both B and T cell epitopes, or conjugating the peptide to a carrier protein such as KLH (Regenmortel, 2001).

As used herein, the term "peptide" refers to linear or cyclic or branched compounds containing amino acids, amino acid equivalents or other non-amino groups, while still retaining the desired functional activity of a peptide. Peptide equivalents can differ from conventional peptides by the replacement of one or more amino acids with related organic acids such as p-aminobenzoic acid (PABA), amino acid analogs, or the substitution or modification of side chains or functional groups. Peptide equivalents encompass peptide mimetics or peptidomimetics, which are organic molecules that retain similar peptide chain pharmacophore groups as are present in the corresponding peptide. The term "peptide" refers to peptide equivalents as well as peptides.

It is to be understood that limited modifications can be made to a peptide without destroying its biological function. Thus, modifications of the peptides of the present invention that do not completely destroy their ability to generate anti-GD2 antibodies are within the definition of the compound claims as such. Modifications can include, for example, additions, deletions, or substitutions of amino acid residues.

As used herein, the term "cyclic peptide" refers to a peptide having an intramolecular bond between two non-adjacent amino acids. The cyclization can be effected through a covalent or non-covalent bond. Intramolecular bonds include, but are not limited to, backbone to backbone, side-chain to backbone and side-chain to side-chain bonds.

Specific peptides of the present invention can be isolated by a variety of methods based on their ability to bind to Anti-GD2 antibodies. For example, peptides characterized by specific anti-GD2 binding activity may be identified by screening a large collection, or library, of random linear peptides or cyclic peptides of interest. Cyclic peptide libraries include, for example, tagged chemical libraries comprising peptides and peptidomimetic molecules. Peptide libraries also comprise those generated by phage display technology. Phage display technology includes the expression of peptide molecules on the surface of phage as well as other methodologies by which a protein ligand is or can be associated with its encoding nucleic acid.

A phage display peptide library is a phage library that is designed to display a pool of peptides composed of random amino acid sequences on filamentous phage. Many phage display peptide libraries are known to contain more than $10^9$ different peptides in each library (Scott, et al. 1990; Bonnycastle, et al. 1996). A peptide that binds to the antigen recognition site of the antibody is expected to have a 3D structure similar to the original antigen. By panning a phage display peptide library with anti-GD2 ganglioside mAb, GD2 ganglioside peptide mimics, which specifically bind to the anti-GD2 ganglioside mAb can be isolated. Phage display peptide libraries have been shown to be useful in isolating peptide mimics of many different antigens, such as GD1a ganglioside (Ishikawa, et al. 1998), Lewis antigens (Luo, et al. 1998; Qiu, et al. 1999), MUC1 (Apostolopoulos, et al. 1999), E-selectin ligand (Fukuda, et al. 2000), anti-HER2/neu antibody (Park, et al. 2000), and capsular polysaccharide from *Streptococcus pneumoniae* (Lesinski, et al. 2001).

Methods for the production of phage display libraries, including vectors and methods of diversifying the population of peptides which are expressed, are well known in the art. (See, for example, Smith and Scott, Methods Enzymol. 217: 228–257 (1993); Scott and Smith, Science 249: 386–390 (1990); and Huse, WO 91/07141 and WO 91/07149, each of which is incorporated herein by reference; see, also, Example 1). Cyclic peptide libraries also are well known in the art (see, for example, Koivunen et al., Methods Enzymol. 245: 346–369 (1994)). These or other well known methods can be used to produce a phage display library, from which peptides of the invention can be isolated using a variety of assays for binding to Anti-GD2 antibodies. Other methods for producing GD2 peptide mimics include, for example, rational design and mutagenesis.

Peptide mimics of GD2 ganglioside can be isolated by panning phage display peptide libraries with anti-GD2 ganglioside such as mAbs 3F8, 5F11, and KM666 that recognize different epitopes on GD2 ganglioside. Anti-GD2 ganglioside mAbs can be used to isolate phage that display antibody reactive peptides. After phage panning, the binding ability of isolated phage colonies to anti-GD2 ganglioside mAbs is tested with immunoscreening and further confirmed by ELISA. Anti-GD2 antibody reactive phage clone and the same phage without displaying peptides, can be utilized as a positive and a negative controls respectively in the immunoscreening and ELISA. In the positive phage clones, the DNA inserts that encode the antibody reactive peptides can be sequenced. Peptides can be synthesized based on the sequences of the DNA inserts. The synthesized peptides are tested in ELISA to determine their binding reactivity with corresponding anti-GD2 ganglioside mAbs. The ability of synthetic peptides to inhibit the binding of anti-GD2 ganglioside mAbs to GD2 ganglioside can be tested in an inhibition assay with GD2-positive cell lines. The synthetic peptides that inhibit or block the binding of anti-GD2 ganglioside mAbs to GD2 ganglioside can be tested as active immunotherapy candidates.

Panning phage display peptide libraries (such as LX-8 and X15) with anti-GD2 ganglioside mABs can be performed by routine procedures. For example, panning can be performed in 96-well microtiter plates (Falcon, Becton Dickinson, Lincoln Park, N.J.) as described previously (Bonnycastle, et al. 1996). A suitable amount of anti-GD2 ganglioside mAbs (0.5–5 µg/well) can be immobilized on an anti-mouse IgG (1+2a+2b+3) Fc' fragment coated 96-well microtiter plate. Phage display peptide libraries ($10_{12}$virions/well) can be added to the anti-GD2 ganglioside mAb coated plates and incubated for a suitable period of time to effect specific binding (4° C. for 4 hours). After the incubation, the bound phage can be eluted. The eluted phage is incubated in wells coated with anti-mouse IgG (1+2a+2b+3) Fc' fragment antibody at 4° C. for an additional 1–2 hours to eliminate phage that bind to the anti-mouse IgG antibody. Phage in the supernatant can be amplified (in E. coli K91kan prepared as described by Smith, et al. 1993) and used for subsequent rounds of panning. Phage enrichment after each round of panning can be determined by spot titering on NZY plates containing tetracycline (20 µg/ml), as described by Smith and Scott (Smith, et al. 1993).

The binding ability of phage clones isolated following subsequent rounds of panning with anti-GD2 ganglioside mAbs can be examined by immunoscreening (Valadon, et al. 1996) with labeled (biotinylated) anti-GD2 ganglioside mAb. The binding activity of positive phage clones to anti-GD2 ganglioside mAbs can also be confirmed by ELISA. The procedures of immunoscreening are known to those skilled in the art (see Christian, et al. 1992). Briefly, phage clones on NZY plates can be transferred onto nitrocellulose membranes. The nitrocellulose membranes are incubated with labeled (biotinylated) anti-GD2 ganglioside mAbs in a suitable buffer (TNT7.5 buffer and 20% FCS for 2 hours). The membranes are washed and then incubated with a detecting agent (such as horseradish peroxidase (HRP)-conjugated streptavidin for 30 minutes). After incubation, antibody bound phage clones can be detected by standard methods. Positive phage clones identified by immunoscreening can be cultured in multi-well plates. The phage supernatants can be collected and subjected to ELISA.

For sequencing of the DNA inserts from phage clones reacting with anti-GD2 ganglioside mAbs, double stranded DNA is extracted by using commercially available kits (QIA prep. Spin, Miniprep kit, Qiagen Inc., Valencia, Calif.) from phage infected E. coli culture. The DNA sequencing can be performed with suitable primers (such as 5'-GCCAATAGTAGCCAACGA-3' (SEQ ID NO:9), which is complementary to the synthetic pVIII gene and locates at more than 90 bp. downstream of the DNA inserts). DNA sequencing is carried out by standard techniques.

Peptides identified according to this invention can be tested for their ability to bind to anti-GD2 antibodies and to generate anti-GD2 antibodies. The peptides of the present invention can be synthesized using methods well known in the art. Such methods include recombinant DNA methods and chemical synthesis. Recombinant methods of producing a peptide through expression of a nucleic acid sequence encoding a peptide in a suitable host cell are well known in the art, such as is described in Sambrook et al., Molecular Cloning: A Laboratory Manual, 2nd Ed, Vols 1 to 3, Cold Spring Harbor, N.Y. (1989), which is incorporated herein by reference.

Peptides of the invention can also be produced by chemical synthesis, for example, by the solid phase peptide synthesis of Merrifield (Merrifield et al., J. Am. Chem. Soc., 85:2149 (1964), incorporated herein by reference). Standard solution methods well known in the art also can be used to synthesize a peptide of the present invention (see, for example, Bodanszky, M., Principles of Peptide Synthesis (Springer-Verlag, 1984), which is incorporated herein by reference). Newly synthesized peptides can be purified, for example, by high performance liquid chromatography (HPLC), and can be characterized using, for example, mass spectrometry or amino acid sequence analysis.

A newly synthesized linear peptide can be cyclized by the formation of a bond between reactive amino acid side chains. For example, a peptide containing a cysteine-pair, or any of the cysteine analogs can be synthesized, and a disulfide bridge can be formed by oxidizing the peptide with 0.01 M $K_3Fe(CN)_6$ at pH 8.4. Alternatively, a lactam, a lysinonorleucine or a dityrosine bond can be formed. Methods for forming these and other bonds are well known in the art and are based on well established principles of chemical reactivity (Morrison and Boyd, Organic Chemistry, 6th Ed. (Prentice Hall, 1992), which is incorporated herein by reference).

A peptide of the present invention also can be cyclized by forming a peptide bond between non-adjacent amino acid residues as described, for example, by Schiller et al., Int. J. Pept. Prot. Res. 25:171 (1985), which is incorporated herein by reference. Peptides can be synthesized on the Merrifield resin by assembling the linear peptide chain using Nα-Fmoc-amino acids and Boc and tertiary-butyl proteins. Following release of the peptide from the resin, a peptide bond can be formed between the amino and carboxyl termini.

The peptides made according to the present invention can be used for active immunotherapy. Peptides can be administered to individuals in need of treatment according to immunization methods known to those skilled in the art. The peptides can be administered alone or in combination with adjuvants in suitable pharmaceutical carriers. Immune response can be monitored by detecting the presence of anti-GD2 antibodies in the serum. While a detectable immunological response is likely to be beneficial, efficacy can also be deduced by an improvement in symptoms or control of growth of the tumor.

The peptides of the present invention can also be used in conjunction with other therapies. For example, the present peptides can be administered following radiation therapy or chemotherapy. It can also be used for prophylactic or therapeutic treatment for recurring tumors.

The following examples are presented for the purposes of illustration and are not intended to be restrictive in any way.

EXAMPLE 1

This embodiment demonstrates the isolation of GD2 peptide mimics. Eight peptide mimics, J51, J50, J10ab, J2gh, J2gh, J8C, J8D, and J8G, have been isolated by panning phage display peptide libraries, PVIII LX8 and PVIII X15, with anti-GD2 ganglioside mAb 3F8. For isolating peptide mimics, mAb 3F8 was immobilized on a 96 well plate by a goat anti-mouse Fc region antibody, which was coated on the plate by 0.1 M $NaHCO_3$ pH 9.6. The antibody-coated plate was blocked by a blotto solution at room temperature for 2 hours. A 50 µl of blotto and 100 µl $10^{12}$ virions TBS solution (PVIII LX8 or PVIII X15 libraries) was added to the blocked plate and incubated in a humidified box at 4° C. for 4 hours. After wash with TBX for six times, the bound phage was eluted by 35 µl elution buffer at room temperature for 10 min. The eluted phage was mixed with 6.6 µl neutralizing solution and then added with 5 µl $5 \times 10^9$/ml starved K91kan (E. coli) cells. The mixture was incubated at room temperature for 15 min. The mixture was added 133 µl 0.2 µg/ml tetracycline super broth and incubated in a humidified box at 37° C. for 40 min with shaking at 150 rpm. A 20 µl 150 µg/ml tetracycline super broth was added to the mixture and the mixture was incubated in a humidified incubator at 37° for 20 hours. The mixture was then centrifuged at 4000 rpm for 30 min and the SNT of the mixture is stored at 4° C. for next round of panning. The panning procedure was repeated for at least two additional times to eliminate the non-specific binding of phage to mAb 3F8. After 3–4 panning, phage infected K91kan cells are titrated on 20 µg/ml of tetracycline NZY agar plates. Positive clones were isolated by immunoscreening and confirmed by reverse ELISA with mAb 3F8. The DNA sequences expressing the mAb 3F8 binding peptide on phage were sequenced. The DNA sequences were translated to peptides and synthesized. Positive phage clones were isolated after four rounds of panning of phage display peptide libraries X15 and LX8 with anti-GD2 ganglioside mAb 3F8. Eight different peptides, J10ab, J2gh, J51, J50, J83, J8C, J8D, and J8G were identified from the positive phage clones (Table 1).

TABLE 1

| SEQ ID NO. | Peptide Name | Sequence |
|---|---|---|
| | PVIII LX8 Library | |
| 1 | J83 | ECVEQGKFMYCA |
| 2 | J8C | KCDPYTLHHYCW |
| 3 | J8D | SCLEQEKWYGCI |
| 4 | J8G | YCTPYDVSIGCR |
| | PVIII X15 Library | |
| 5 | J51 | DCFRGDPYQPKWRLC |
| 6 | J50 | SLPEDRYEDGWIFKP |
| 7 | J10ab | ACREGPPYYFCPSL |
| 8 | J2gh | PTGRCEVHCSNSNTT |

The synthesized peptides were tested with reverse ELISA and inhibition assay with mAb 3F8. The peptides, which can inhibit the binding of anti GD2 antibody to GD2 ganglioside bearing cell lines, are considered as peptide mimics. For example, J51, isolated from the PVII X15 library, inhibited the binding of mAb 3F8 to GD2 ganglioside bearing melanoma cells. Peptide J51 contains HLA-B7 and HLA-DRB1 binding motifs. These results suggest that peptide J51 can serve as a GD2 gaglioside peptide mimic and can be used for inducing both humoral and cellular responses to GD2 ganglioside.

EXAMPLE 2

This embodiment demonstrates that the peptide mimics generated by the present invention can be used to generate an anti-GD2 response. A cyclic peptide J51 (cJ51), which mimics the structure of GD2 ganglioside (GD2), has been shown to inhibit the binding of anti-GD2 mAb 3F8 to GD2 (+) human melanoma cells (Example 1). In order to study the ability of cJ51 to induce anti-GD2 IgG antibody responses in mice, cJ51 was conjugated to a carrier protein, keyhole limpet hemocyanin (KLH), to increase its immunogenicity. A group of 10 female BALB/c mice were immunized with cJ51-KLH (50 mg/mouse) and Freund's adjuvant (1:1 ratio) at two week intervals. Mice were bled 10 days after each immunization. The anti-GD2 Ig G antibody responses in the sera after each immunization were tested in Enzyme-linked Immunosorbent Assay (ELISA) with GD2 (+) cells (HTB63) and a negative control, GD2 (−) cells (LG2). After the fifth immunization, the sera (1:30 dilution) from immunized mice displayed a significantly higher reactivity with GD2 (+) cells than GD2 (−) cells (P=0.0001). As shown in FIG. 1, these sera display a significantly higher reactivity with GD2 (+) cells than preimmune sera (1:30 dilution) (P=0.00013). This indicates that the peptides identified and isolated according to the present invention can be used to generate an immure response to GD2.

While the invention has been described by the examples presented herein, it should be understood that various modifications can be made without departing from the spirit of the invention. Such modifications are intended to be included within the scope of the claims.

REFERENCES

1. Apostolopoulos, V., Sandrin, M. S., and McKenzie, I. F. Carbohydrate/peptide mimics: effect on MUC1 cancer immunotherapy. J. Mol. Med. 77:427–436, 1999.
2. Bonnycastle, L. L., Mehroke, J. S., Rashed, M., Gong, X. and Scott, J. K. Probing the basis of antibody reactivity with a panel of constrained peptide libraried displayed by filamentous phage. J. Mol. Biol. 258:747–762, 1996.
3. Chapman, P. B., Morrisey, D., Panageas, K. S., Williams, L., Lewis, J. J., Israel, R. J., Hamilton, W. B., and Livingston, P. O., Vaccine with a bivalent GM2 and GD2 ganglioside conjugate vaccine: a trial comparing doses of GD2-keyhole limpet hemocyanin. Clin. Cancer Res. 6:4658–4662, 2000.
4. Chianese-Bullock, K. A. and Slingluff, C. Peptide vaccines for cancer. In: Principles and practice of biologic therapy of cancer (update). 3: 1–16, 2002. Rosenberg, S. A. edit.
5. Cheung, N. K, Guo, H. F., Heller, G., and Cheung, I. Y. Induction of Ab3 and Ab3' antibody was associated with long-term survival after anti-G(D2) antibody therapy of stage 4 neuroblastoma. Clin. Cancer Res. 6:2653–2660, 2000
6. Christian, R. B., Zuckernann, R. N., Kerr, J. M., Wang, L., and Malcolm, B. A. Simplified methods for construction, assessment and rapid screening of peptide libraries in bacteriophage. J. Mol. Biol. 227:711–718, 1992.
7. Fukuda, M. N., Ohyama, C., Lowitz, K., Matsuo, O., Pasqualini, R., Ruoslahti, E., and Fukuda, M. A peptide mimic of E-selectin ligand inhibits sialyl Lewis X-dependent lung colonization of tumor cells. Cancer Res. 60: 450–456, 2000.
8. Hsueh, E. C. Tumour cell-based vaccines for the treatment of melanoma. Biodrugs. 15:713–720, 2001.
9. Ishikawa, D., Kikkawa, H., Ogino, K., Hirabayashi, Y., Oku, N., and Taki, T. GD1alpha-replica peptides functionally mimic GD1 alpha, an adhesion molecule of metastatic tumor cells, and suppress the tumor metastasis. FEBS Lett. 441:20–24. 1998.
10. Kramer, K., Gerald, W. L., Kushner, B. H., Larson, S. M., Hameed, M., and Cheung, N. K. Disialoganglioside GD2 loss following monoclonal antibody therapy is rare in neuroblastoma. Med. Pediatr. Oncol. 36:194–196,2001.
11. Kushner, B. H., Kramer, K., and Cheung, N. K. Phase II trial of the anti-GD2 monoclonal antibody 3F8 and granulocyte-macrophage colony-stimulating factor for neuroblastoma. J. Clin. Oncol. 19:4189–4194,2001.
12. Lesinski, GB., Smithson, SL., Srivastava, N., Chen, D., Widera, G., and Westerink, MA. A DNA vaccine encoding a peptide mimic of *Streptococcus pneumoniate* serotyp 4 capsular polysaccharide induces specific anti-carbohydrate antibodies in Balb/c mice. *Vaccine.* 19, 1717–26(2001).
13. Luo, P., Canziani, G., Cunto-Amensty, G., and Kieber-Emmons, T. A molecular basis for functional peptide mimicry of a carbohydrate antigen. *J. Bio Chem.* 275, 16146–54 (2000).
14. Murray, J. L., Cunningham, J. E., Brewer H., Mujoo, K., Zukiwski, A. A., Podoloff, D. A., Kasi, L. P., Bhadkamkar, V., Fritsche, H. A., and Benjamin, R. S. Phase I trial of murine monoclonal antibody 14G2a administered by prolonged intravenous infusion in patients with neuroectodermal tumors. J. Clin. Oncol. 12:184–193,1994.
15. Park, B. W., Zhang, H. T., Wu, C., Berezov, X., Dua, R., Wang, Q., Kao, G., O'Rourke, D. M., Green, M. I., and Murali, R. Rationally designed anti-HER2/neu peptide mimetic disables P185HER2/neu tryosine kinases in vitro and in vivo. Nature Biotechnol. 18:194–198, 2000.
16. Philip, P. A., and Flaherty, L. E. Biochemotherapy of melanoma. Curr. Oncol. Rep. 2:314–321, 2000.
17. Qiu, J., Luo, P., Wasmund, K., Steplewski, Z., and Kieber-Emmons, T. Towards the development of peptide mimotopes of carbohydrate antigens as cancer vaccines. *Hybridoma.* 18, 103–112 (1999).
18. Regenmortel, M. Antigenicity and immunogenicity of synthetic peptides. Biol 29:209–213, 2001.
19. Saleh, M. N., Khazaeli, M. B., Wheeler, R. H., Dropcho, E., Liu, T., Urist, M., Miller, D. M., Lawson, S., Dixon, P., and Russell, C. H. Phase I trial of the murine monoclonal anti-GD2 antibody 14G2a in metastatic melanoma Cancer Res. 52:4342–4347, 1992.
20. Scott, J. K. and Smith, G. P. Searching for peptide ligands with an epitope library. Science. 249:386–390, 1990.
21. Slart, R., Yu, A. L., Yaksh, T. L., and Sorkin, L. S. An animal model of pain produced by systemic administration of an immunotherapeutic anti-ganglioside antibody. Pain. 69:119–125, 1997.
22. Sorkin, L. S., Yu, A. L., Junger, H., and Doom, C. M. Antibody directed against GD(2) produces mechanical allodynia, but not thermal hyperalgesia when administered systemically oe intrathecally despite its dependence on capsaicin sensitive afferents. Brain Res. 930:67–74, 2002.
23. Tai, T., Cahan, L. D., Tsuchida, T., Saxton, R. E., Irie, R. F., and Morton, D. L. Immunogenicity of melanoma-associated ganglioside in cancer patients. Int. J. Cancer. 35:607–612, 1985.
24. Takahashi, T., Johnson, T. D., Nishinaka, Y., Morton, D. L., and Irie, R. F. IgM anti-ganglioside antibodies induced by melanoma cell vaccine with survival of melanoma patients. J. Investig. Dermatol. 112:205–209, 1999.
25. Valadon, P. and Scharff, M. D. Enhancenment of ELISAs for screening peptides in epitope phage display libraries. J. Immunol. Methods 197:171–179, 1996.
26. Wang, X., Luo, W., Foon, K. A., and Ferrone, S. Tumor associated antigen (TAA) mimicry and immunotherapy of malignant diseases from anti-idiotypic antibodies to peptide mimics. Cancer Chemother. Biol. Response Modif. 19:309–326, 2001.
27. Yu, A. L., Uttenreuther-Fischer M. M., Huang, C. S., Tsui, C. C., Gillies, S. D., Reisfeld R. A., and Kung, F. H. Phase I trial of a human-mouse chimeric anti-disialoganglioside monoclonal antibody ch14.18 in patients with refractory neuroblastoma and osteosarcoma. J. Clin. Oncol. 16:2169–2180, 1998.

What is claimed is:

1. An isolated and purified peptide which blocks the binding of an anti-GD2 antibody to a tumor cell expressing GD2 ganglioside and is capable of eliciting antibodies reactive against GD2 ganglioside, wherein the sequence of the peptide is SEQ ID NO:5.

2. An antigenic composition comprising a peptide which blocks the binding of an anti-GD2 antibody to a tumor cell bearing GD2 ganglioside and is capable of eliciting antibodies reactive against GD2 ganglioside and a pharmaceutically acceptable carrier, wherein the peptide has a sequence of SEQ ID NO:5.

3. The antigenic composition of claim 2 further comprising an adjuvant.

* * * * *

UNITED STATES PATENT AND TRADEMARK OFFICE
Certificate

Patent No. 6,939,948 B1            Patented: September 6, 2005

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Soldano Ferrone, Buffalo, NY (US); Chun-Yen Tsao, Grand Island, NY (US); Xinhui Wang, Williamsville, NY (US); Wei Luo, Getzville, NY (US); Nai-Kong V. Cheung, Purchase, NY (US); and Jeff Chi-Feng Hsu, Tonawanda, NY (US).

Signed and Sealed this Ninth Day of January 2007.

WILLIAM R. DIXON, Jr.
*Special Program Examiner*
Art Unit 1600